United States Patent
Kothwala et al.

(10) Patent No.: US 12,419,994 B2
(45) Date of Patent: Sep. 23, 2025

(54) PROCESS FOR PREVENTION OF DEGRADATION AND DEGENERATION OF TISSUE USED IN BIOPROSTHESIS

(71) Applicant: Meril Life Sciences PVT LTD, Vapi (IN)

(72) Inventors: Deveshkumar Mahendralal Kothwala, Surat (IN); Amirhamzah Mahmadiqbal Shaikh, Valsad (IN); Pramod Kumar Minocha, Vapi (IN)

(73) Assignee: Meril Life Sciences PVT LTD, Vapi (IN)

( * ) Notice: Subject to any disclaimer, the term of this patent is extended or adjusted under 35 U.S.C. 154(b) by 764 days.

(21) Appl. No.: 17/441,488

(22) PCT Filed: Dec. 27, 2019

(86) PCT No.: PCT/IN2019/050959
§ 371 (c)(1),
(2) Date: Sep. 21, 2021

(87) PCT Pub. No.: WO2020/208644
PCT Pub. Date: Oct. 15, 2020

(65) Prior Publication Data
US 2022/0176018 A1 Jun. 9, 2022

(30) Foreign Application Priority Data
Apr. 10, 2019 (IN) .............................. 201921014508

(51) Int. Cl.
*A61F 2/24* (2006.01)
*A61L 27/36* (2006.01)

(52) U.S. Cl.
CPC ........ *A61L 27/3687* (2013.01); *A61F 2/2415* (2013.01); *A61L 27/3625* (2013.01); *A61L 2400/02* (2013.01); *A61L 2430/20* (2013.01); *A61L 2430/40* (2013.01)

(58) Field of Classification Search
CPC .................................................. A61L 27/3687
See application file for complete search history.

(56) References Cited

U.S. PATENT DOCUMENTS

| | | | |
|---|---|---|---|
| 6,322,593 B1 | 11/2001 | Pathak et al. | |
| 6,878,168 B2 | 4/2005 | Carpentier et al. | |
| 7,559,953 B2 * | 7/2009 | Sarac | A61L 27/507 623/23.72 |
| 9,314,420 B2 * | 4/2016 | Ahlfors | A61L 27/3683 |
| 2006/0154230 A1 * | 7/2006 | Cunanan | A01N 1/02 435/1.1 |
| 2007/0020248 A1 * | 1/2007 | Everaerts | A61L 27/3683 435/459 |
| 2008/0302372 A1 | 12/2008 | Davidson | |

* cited by examiner

*Primary Examiner* — Megan Y Wolf
(74) *Attorney, Agent, or Firm* — Kunzler Bean & Adamson

(57) ABSTRACT

There is disclosed a process for treatment to avert enzymatic degradation and tissue degeneration of bovine pericardium tissue, used for making bioprosthesis for implant application, comprising the steps of collecting and harvesting raw bovine pericardial tissue; chemically cross-linking the rinsed tissue to generate fixed tissue; laser cutting said fixed tissue to produce tissue leaflet; chemically treating said tissue leaflet with AAS; chemically sterilising and storing the fixed bovine pericardium tissue to maintain the structural integrity and characteristics; and wherein all the above steps are carried out in a low-oxygen and controlled temperature environment.

10 Claims, 4 Drawing Sheets

PROCESS FOR PREVENTION OF DEGRADATION AND DEGENERATION OF TISSUE USED IN BIOPROSTHESIS

FIELD OF INVENTION

The present invention relates to a process to avert enzymatic degradation and tissue degeneration of bovine pericardium tissue, used in bioprosthesis for implant application and bioprosthesis made thereby. The method of the present invention helps in manufacturing integrated fixed bovine pericardial bioprosthesis.

BACKGROUND OF THE INVENTION

Tissue integrity is vitally important feature for the bioprosthesis made out of this for implant applications. Non limiting example of such bioprosthesis could be heart valves, stent grafts or any other such as surgical patches, etc. Under normal environment of temperature, humidity, air or some traditional fixation methods, it is always a challenge to achieve tissue integrity and its stability. Under such conditions, normal tissue, treated tissue or any other treated tissue develop cracks, tanned in colour, loses its mechanical strength including elasticity & characteristics, etc. over a period of time.

Heart valve replacement or repair with biological origin material lost its attraction over a period of time due to various problems associated with the biological materials such as calcification, durability, storage of device and also poor performance in comparison to mechanical devices. Poor performance of bioprosthesis is due to tissue degeneration and calcification, the pathophysiology remains still unclear for both. Calcification refers to the deposition of calcium phosphate salt and associated minerals on tissue surface, phospholipid-based cell membranes are known to be a key material for calcification. Tissue degradation resulting in mechanical failure of heart valves initiates with collagen fiber disruption over a period of time that result in stress concentrations forming at weak points in bioprosthesis. Fiber disruption, orientation changes, fatigue-induced fiber damage and degenerative changes to apparent mechanical properties have been found to correlate with Extra Cellular Matrix (ECM) component loss such as glycosaminoglycan leeching and elastin degeneration. It has also been shown that oxidative stress may also play a significant role in tissue leaflet structural degradation. Glutaric dialdehyde ($CHO(CH_2)_3CHO$) used for the cross-linking of tissue is also known to play a role in calcification. Specifically, the free aldehyde groups and carboxylic acids that did not form cross-links with tissue collagen are understood to have cytotoxicity and augment tissue calcifications most.

U.S. Pat. No. 6,878,168 discloses a method for mitigating post-implantation calcification of a bioprosthetic material, said method comprising the steps of:
- (a) heating a glutaraldehyde solution having a pH of between 7.2-7.8 to a first temperature above 20° C. for a first period of time of at least one hour until the pH of the glutaraldehyde solution has been reduced to between 5-7; and
- (c) contacting a quantity of biological tissue that contains connective tissue protein with the pH-reduced glutaraldehyde solution for a second period of time of at least one hour.

U.S. Pat. No. 7,559,953 discloses a method of preparing a fixed biological tissue, the method comprising:
- (a) harvesting at least one layer of biological tissue, the biological tissue being selected from the group consisting of pericardial tissue, peritoneal tissue, and pleural tissue, the layer of biological tissue comprising an inner lining of a serous membrane and an outer lining of associated fascia;
- (b) shaping the biological tissue, wherein the shaping comprises trimming and shaping the harvested layer of biological tissue to a desired size and configuration;
- (c) at least partially cross-linking the biological tissue by contacting the biological tissue with a solution containing at least one cross-linking agent;
- (d) sterilizing the biological tissue by contacting the at least partially cross-linked biological tissue with a solution containing an alcohol; and
- (e) inactivating prions in the sterilized biological tissue, the prions in the biological tissue being inactivated by contacting the sterilized biological tissue with a basic solution having a molar concentration of about 0.5 M to about 4.0 M; whereby steps (a)-(e) are performed sequentially.

U.S. Pat. No. 6,322,593 discloses a method for treating biological tissue is provided in which a cross-linked biological tissue containing free aldehyde groups is reacted with a suitable neutralization agent in order to chemically block the aldehyde groups from reactivity toward cellular proteins. Also provided is the cross-linked biological tissue so produced which is substantially free of reactive aldehyde groups and, as a result, exhibits reduced toxicity and improved biocompatibility.

However, the above solutions cannot eradicate the problem of tissue calcification and degeneration.

Prosthetic heart valves, used for the definitive treatment of diseased and dysfunctional native heart valves, have been in use since the mid 1960s. They are broadly divided into mechanical heart valves (MHVs) and bioprosthetic heart valves (BHVs). MHVs are made of synthetic material (e.g., polymers, metal, and carbon), whereas BHVs are made of biologic tissues which are mounted on a fabric covered metal frame. MHVs are more durable, but their thrombogenicity and need for long-term anticoagulant therapy make them unsuitable for patients in some age groups especially older age groups. In contrast, BHVs are safe to implant, functionally similar to the native aortic valve, do not require long-term anticoagulant therapy, and are hence associated with reduced risk of haemorrhage. However, conventional fixation methods associated with degeneration of fixed tissue internal structure such as collagen fiber and other Extra Cellular Components (ECM). Tissue degradation occurs due to collagen fiber disruption. The instability of Glutaric dialdehyde ($CHO(CH_2)_3CHO$) bonds results allowing collagen fibers to slowly lose structural integrity. Therefore, there is a need of providing an improved method of tissue treatment and improved bioprosthesis made from such treated tissue.

In the instant invention, method to make integrated, with improved durability, stability and with enhanced shelf life of fixed tissue is disclosed.

OBJECT OF INVENTION

It is the principal object of the present invention is to provide autolysis free and integrated fixed bovine tissue used for manufacturing of bioprosthesis.

Another object of the present invention is to provide integrated fixed tissue manufacturing method under low-oxygen environment and in low concentration of Glutaric dialdehyde storage solution to maintain fundamental characteristics of fixed bovine pericardial tissue.

It is another object of the present invention is to provide a bovine pericardial tissue treated with basic buffers and repeatedly washed during chemical treatment under low-oxygen atmosphere cabinet, thus averting enzymatic degradation of fixed tissue.

Yet another object of the present invention is to provide a fixed tissue having negligible carboxylic acid content over surface, reduced calcification sites thus reduces calcification of fixed pericardial tissue.

It is a further object of the present invention is to provide fixed tissue which is autolysis free, mechanically and chemically stable and durable resulting in ultimately enhanced bioprosthesis integrity and so the shelf life.

It is another object of the invention is to provide laser cut tissue leaflets which is cut into transverse mode to avoid tear and wear of heart valve leaflets.

SUMMARY OF INVENTION

Accordingly the present invention provides a process for treatment to avert enzymatic degradation and tissue degeneration of bovine pericardium tissue, used for making bioprosthesis for implant application, comprising the steps of collecting and harvesting raw bovine pericardial tissue; chemically cross-linking the rinsed tissue to generate fixed tissue; laser cutting said fixed tissue to produce tissue leaflet; chemically treating said tissue leaflet with AAS; chemically sterilising and storing the fixed bovine pericardium tissue to maintain the structural integrity and characteristics; and wherein all the above steps are carried out in a low-oxygen and controlled temperature environment.

Preferably said low-oxygen environment has an oxygen content of 5-15%.

More preferably the low-oxygen environment has an oxygen content of 8-10%.

The said controlled temperature is in the range of 18-20° C. during processing and 8-10° C. during storing.

Preferably, said rinsing with chilled saline solution follows every chemical and physical treatment step till sterilisation and storing. Rinsing with chilled saline solution is carried out by providing continuous shower of chilled saline solution under low-oxygen and controlled temperature environment.

Preferably the chemical cross-linking is carried out using 0.625% Glutaric dialdehyde buffered solution.

Preferably the chemical cross-linking is carried out with continuous circular flow of glutaric dialdehyde at rate of 0.8 L/min.

Preferably the cross-linking step is carried out for 35 minutes.

Preferably said storing of fixed pericardium tissue is carried out using 0.625% Glutaric dialdehyde buffered solution.

The invention also provides a process for making bioprosthesis for implant application, comprising the steps of collecting and harvesting raw bovine pericardial tissue; chemically crosslinking the rinsed tissue to generate fixed tissue; laser cutting said fixed tissue to produce tissue leaflet; chemically treating said tissue leaflet with AAS; chemically sterilising and storing the fixed bovine pericardium tissue to maintain the structural integrity and characteristics; and fabricating bioprosthesis from such fixed tissue under moist condition using sprinkled saline flow; and wherein all the above steps are carried out in a low-oxygen and controlled temperature environment.

The invention also provides a bioprosthesis for implant application manufactured with the treated bovine pericardium tissue by the above method. Preferably, the bioprosthesis is selected from heart valves, stent grafts and surgical patches.

BRIEF DESCRIPTION OF THE ACCOMPANYING DRAWINGS

DETAILED DESCRIPTION OF THE INVENTION

In order to overcome the problem of the prior art, the present invention discloses a method of manufacturing integrated fixed bovine pericardial tissue with enhanced stability, durability and susceptible to longer shelf life. Further, the invention discloses a method for manufacturing integrated fixed bovine pericardial bioprosthesis under low-oxygen environment related to field of cardiovascular repair, reconstruction, specifically heart valve replacement & repair, etc.

It is found that low-oxygen environment aids in enhancing the chemical reactivity of tissue with processing chemicals and avoid putrefactive changes by removing dead colonies, toxic substances, etc; also prevents oxidation stress on fixed tissue and degradation of storage chemical solution.

The process of the invention comprises of collection and harvesting of raw pericardial tissue under hygienic condition and low-oxygen environment with continuous shower of saline, basic salt solution rinsing process, chemical fixation to make stable cross-linked tissue which avert structural deterioration and deprivation, fixed tissue laser cutting processes, aldehyde storage to prevent enzymatic degradation, AAS based liquid chemical sterilization and low concentration storage solution.

The various steps of the process are described hereinbelow.

Raw Pericardium Collection and Harvesting:

The raw bovine pericardium can generally be collected and harvested from the slaughterhouse inspected and approved by the FDA and complies the procedure described as per ISO 13485 and ISO 22442-1, -2, -3.

In one embodiment, raw bovine pericardium is obtained from the local slaughterhouse, placed in chilled phosphate-buffered saline (PBS, 0.1 M, pH 7.4) having temperature range between 2-8° C. and immediately transferred to laboratory for further treatment. Raw tissues rinsed with normal saline and are freed from adherent fat at 18-20° C. temperature.

In another embodiment, raw bovine hearts, with pericardium intact, collected from the FDA approved abattoir where the history and data of an animal is maintained as per standard and regulatory norms. The raw pericardial tissue is dissected and removed from the heart by cutting along the base of the heart, leaving the remaining tissue intact. The raw pericardium tissue having uniform thickness is transferred to the laboratory in buffered saline to maintain tissue structural integrity and electrolytic balance. The raw tissue is rinsed, and trimmed of external fat, adherent material in the laboratory.

Figure 1:
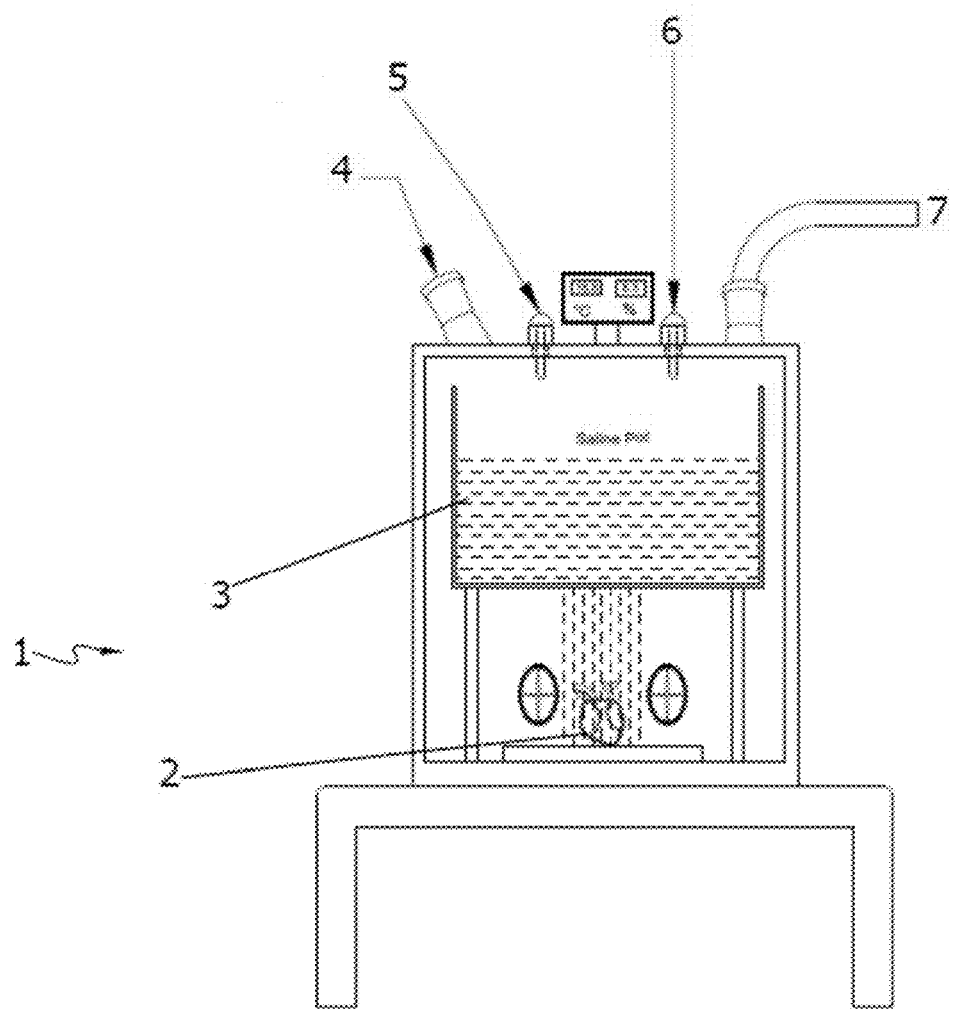
FIG. 1 illustrates an apparatus for continuous shower of chilled saline on heart valve pericardium during collection and harvesting.

In a preferred embodiment, the raw bovine pericardium is collected from the bovine whose upper age limit is below 24 months with healthy condition (Transmissible Spongiform Encephalopathy-TSE/Bovine Spongiform Encephalopathy-BSE level free). The health data and record is monitored and maintained in the slaughterhouse. The bovine heart is immediately transferred into low-oxygen chamber where the temperature of cabinet is controlled to preferably 15-25° C., more preferably 18-20° C. The raw tissue is typically harvested by surgical cutting from animal's heart. It is trimmed or cut to size and washed with de-ionized water, basic salt solution, saline or other suitable washing solution. Continuous shower of chilled saline is maintained while collection and harvesting procedure is performed to avert deprivation and prevent putrefactive changes of living cells. The shower of chilled saline maintains the electrolytic pH balance for such period of time and avoids putrefactive changes in raw tissue FIG. 1 shows an apparatus (1) capable of providing continuous shower of chilled saline on heart valve or heat valve pericardium tissue during collection and harvesting. The device comprising an airtight container having a saline pot (3) which continuous supply of saline water to the collected bovine heart or pericardium tissue (2) kept at a suitable position at a predetermined distance inside the device. A nitrogen inlet (4), temperature analyser (5), an oxygen analyser (6) and a vent line (7) are also provided in the apparatus for maintain suitable low oxygen environment.

The raw bovine pericardium is placed in phosphate-buffered saline (PBS, 0.1 M, pH 7.4±0.2) and immediately transported to laboratory. The entire operation is done preferably within 20-40 minutes; more preferably 30 minutes in low-oxygen environment ranges from 5-15%, preferably at 8-10%. Oxygen content of surrounding environment is measured using conventional oxygen analyser, which has selectable measurement range from 0.1-25% volume O2. Low-oxygen condition prevents oxidative stress on living cells and maintains structural integrity of collagen fibres. Harvested raw tissue is further rinsed it with normal saline and freed from adherent fat. While removing adherent fat and fatty material, continuous shower of phosphate buffer saline is maintained and then stored in chilled 0.9% saline solution at 8-10° C. temperature till fixation is carried out. Use of chilled saline reduces microbial growth by providing antagonist environment for the bacteria and other microorganisms. Due to low temperature in saline, life cycles of microbes is hampered and avoid putrefactive changes in living tissue.

Rinsing Process:

Once adherent material of fats, blood vessels and clots are removed from the pericardial tissue, it is repeatedly rinsed with basic saline salt solution to maintain electrolytic balance and prevents damage to the living cells before cross-linking process. In one embodiment, raw tissue is rinsed with basic saline salt solution for thrice to remove traces of adherent material.

In an embodiment, raw pericardial tissue is rinsed with chilled 0.9% saline solution by putting the tissue in stainless steel (SS) bath at room temperature with relative humidity of 55%. Initially, chilled 0.9% saline solution is poured in a stainless steel bath and bovine pericardium is placed there, which is already trimmed and washed previously while collection. Then, raw pericardial tissue is rinsed repeatedly, till all debris and remaining fatty material washed off. After rinsing process, fresh & chilled saline solution is again poured in SS bath and then rinsed the tissue from both sides.

In a preferred embodiment, the raw bovine pericardium is placed in phosphate-buffered saline (PBS, 0.1 M, pH 7.4±0.2) at 18-20° C. temperature. Further, rinsed the tissue thrice with chilled 0.9% saline and freed from adherent fat to completely remove fatty matter by placing inside SS bath before trimming and cutting of raw tissue. Once, the excess material is removed out and rinsed with chilled 0.9% saline the rinsed pericardial tissue is inspected for holes, damaged surface and thickness of the tissue.

Thickness of the rinsed tissue is measured with conventional thickness gauge. This tissue is again washed with normal saline solution and further subjected to the cross-linking or GA fixation process. Rinsing with chilled 0.9% saline removes bad odour from the living cells and gives enrichment of electrolytic balance to the living cells of the tissue. The entire rinsing process with saline solution is completed within 05-15 minutes, preferably within 09-12 minutes.

Cross-Linking of Rinsed Bovine Pericardial Tissue:

Glutaric dialdehyde fixation is a tissue preservation process used in the manufacture of bioprosthetic heart valves. The objective of cross-linking process is to produce integrated, stable, durable, and biologically inert fixed tissue that is suitable for medical implantation. Collagen, a principle tissue protein, provides strength and resistance to breaking stresses in tissue and plays a critical role in its long-term durability.

Fixation of rinsed bovine tissue is carried out by using aqueous Glutaric dialdehyde solution conventionally, as Glutaric dialdehyde having dual aldehyde groups with highest cross-link stability with collagen fibre composites. Glutaric dialdehyde treatment changes the collagen properties and renders the tissue which is acceptable in the human host. Cross-linking process is shown to increase stability and strength of the fixed pericardial tissue, thus suitable for the fabrication or manufacturing of bioprosthesis.

However, many other cross-linking agents/chemicals can be incorporated for the fixation of rinsed bovine pericardium or any other biological tissue as depicted in below table as fixative to make non-reactive tissue;

TABLE 1

List of cross-linking agent

| Subjected Tissue | Cross-linking Agents |
| --- | --- |
| Rinsed Bovine Pericardium | Glutaric dialdehyde |
| | Formaldehyde |
| | Glutaric dialdehyde acetals |
| | Epoxy compound |
| | Acyl azide |
| | Dye-mediated photo-oxidation |
| | Cyanimide |
| | Carbodiimides |

In one embodiment, fresh aqueous 0.625% Glutaric dialdehyde (CHO(CH$_2$)$_3$CHO) solution is prepared and then vacuum filtered at normal-oxygen environment to remove any unwanted particles.

Figure 2:
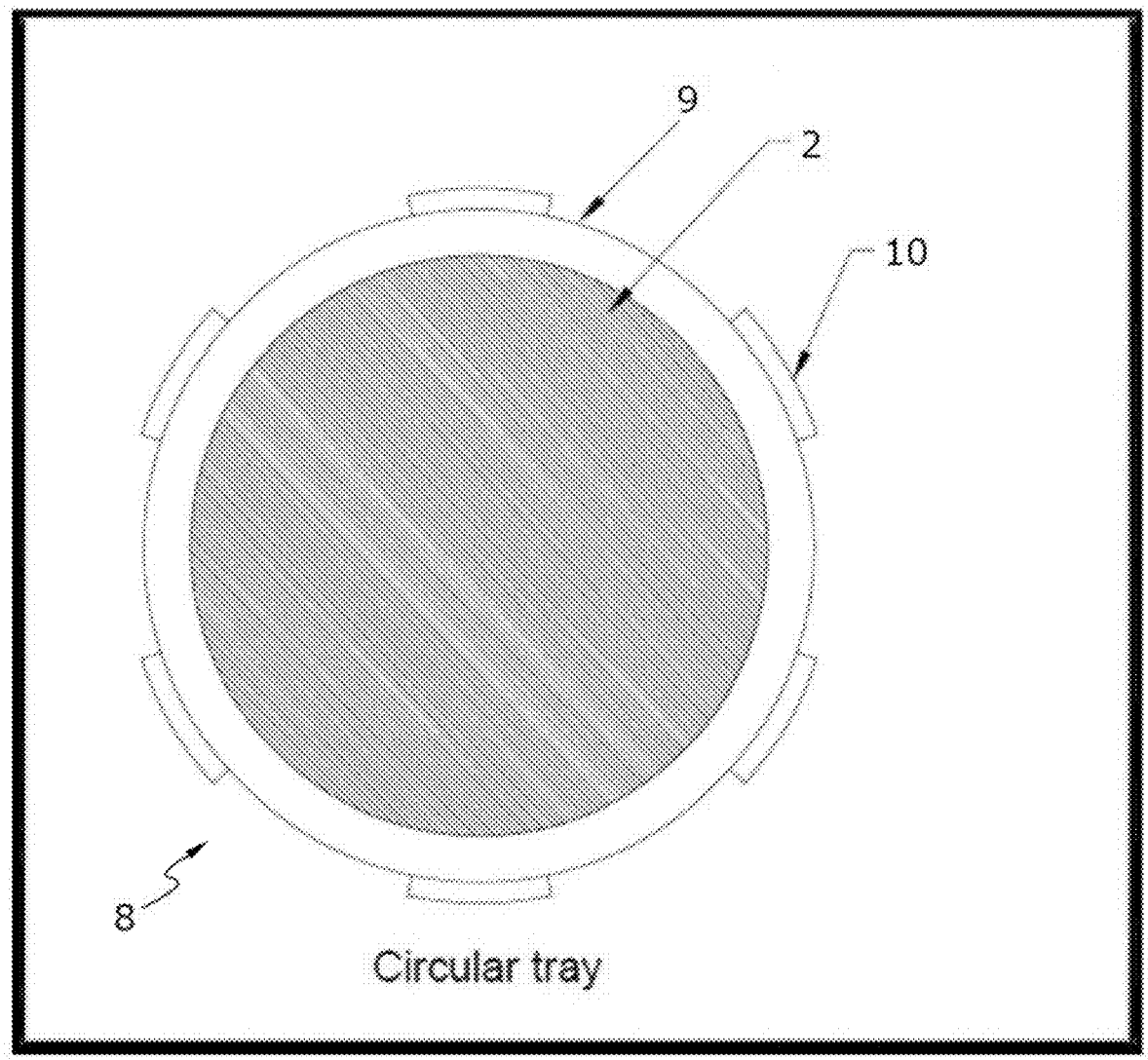
FIG. 2 is a perspective view of circular fixation tray for raw tissue holding purpose during fixation/cross-linking process, in accordance to exemplary embodiment of invention.

FIG. 2 shows a piece of rinsed pericardial tissue (2) positioned on SS tray (8) in a fixation frame (9) with a locking system (10).

Figure 3:
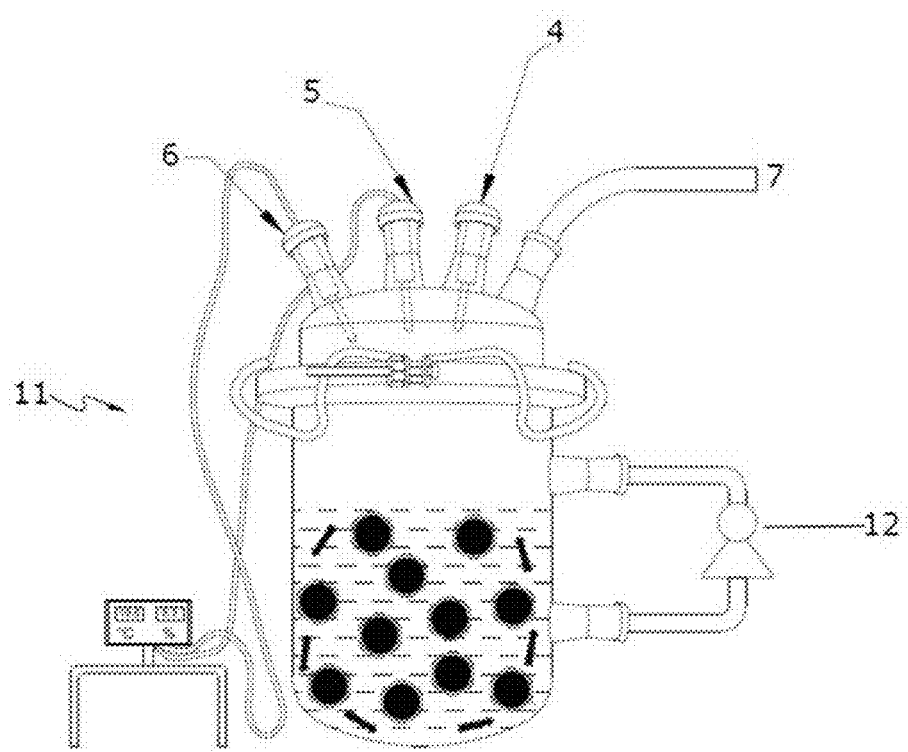
FIG. 3 illustrates fixation flat flange assembly with continuous circular flow of cross-linking solution in accordance to exemplary embodiment of invention.

As shown in FIG. 3, fixation is carried out in Flat Flange (FF) (11) provided with a nitrogen inlet (4), a temperature analyser (5), an oxygen analyser (6), a vent line (7) and a circulatory pump (12).

The circulatory pump is attached at an inlet at one flange of FF tank and outlet of solution at the other end. On another flange, medical grade nitrogen (N$_2$) gas pipe is attached to remove air and oxygen from the FF tank, while oxygen (O$_2$) analyser and temperature sensor are attached to other probes. By purging medical grade N$_2$ gas flow into FF tank, the oxygen level is maintained between 5-15%, preferably 8-10% throughout the process inside the chamber. Temperature and percentage of oxygen content has functional effect on rinsed tissue and cross-linking solution.

Approximately 5 litre solution is poured in a Flat Flange (FF) Tank at normal-oxygen environment of atmosphere. Circulatory pump is connected to the FF Tank for proper circulation of cross-linking solution, as it enhances cross-linking capability with the rinsed tissue and provides stable bonding in the tissue protein with the fixatives. The circulation of solution also provides better adherence/contact of rinsed tissue to upper and lower surface. Also, circulation mechanism enhances floating capability of rinsed bovine pericardium, which is positioned in a fixative frame, and maintained at 18-20° C. temperature for 30 minutes-50 minutes. After that, it is rinsed with 0.9% saline solution to remove unreacted Glutaric dialdehyde and further stored in 0.625%

Glutaric dialdehyde solution for the period of 06 days-10 days at room temperature. After cross-linking process, the resulting tissue becomes golden yellowish in colour having thickness in range between 0.32 mm-0.48 mm. Optionally, other thickness range of tissue such as 0.40 mm-0.55 mm or 0.30 mm-0.50 mm, etc. can achieved utilizing same process.

In a preferred embodiment, cross-linking process utilizes a neutral pressure and continuous circulation of fixatives i.e. Glutaric dialdehyde in low-oxygen chamber that helps to preserve the natural elasticity of the collagen matrix and enhances cross-link stability of collagen molecules present in rinsed bovine tissue. Glutaric dialdehyde used in the process is Analytical grade reagent with assay not less than 25%. Cross-linking process allows Glutaric dialdehyde to form stable cross-link with collagen molecule of lysine chains that result in durable fibrous tissue structures having long-term performance properties suited for bioprosthetic heart valve and pericardial patches application.

Initially, rinsed bovine pericardium is placed in a SS bath containing normal 0.9% saline solution. The rinsed tissue is washed repeatedly, preferably thrice for 03 minutes each at 18-20° C. temperature with saline and positioned in a fixation frame. Place the rinsed tissue piece with the smooth side facing up over the bottom of the fixture i.e. fixative frame. The advantages of placing smooth surface upper side is that it enhances cross-linking aptitude, efficiency and also increase robustness of tissue. While fixing in a frame, rinsed tissue should be firm to make total surface available for in-contact with fixative agents/solution. Excess tissue may be trimmed if necessary. All the frames containing rinsed tissue are placed in a FF tank for cross-linking process.

0.625% Glutaric dialdehyde solution in aqueous medium with water for injection (WFI) as solvent is prepared as depicted in Table-2, in a clean and low-oxygen cabinet to avoid contamination and degradation of Glutaric dialdehyde to uphold its physical and chemical characteristics. The significance to use low-oxygen cabinet for preparation of cross-linking solution is to preserve chemical properties of Glutaric dialdehyde solution by maintaining 18-20° C. working area temperature and prevents contamination with toxins which can affect cross-linking outcome to the rinsed tissue. WFI enhances the Glutaric dialdehyde stability and reduces degradation and avoid any unwanted growth of microorganisms. For cross-linking process, approximately 5 liters of filtered fixative solution is poured in FF tank and 8-10 circular frames containing rinsed tissue are placed. The frame may be left floating in the FF tank. Cross-linking solution remains in circulation to make more effective cross-linking process with rinsed bovine pericardial tissue. The flow rate is maintained to 0.5-2 L/minute, preferably 1.3 L/minute-2.2 L/minute, more preferably 0.8 L/minute-1.1 L/minute. Tissue immersion period is set for approximately 20 minutes-50 minutes, preferably 30 minutes-40 minutes or more preferably 35 minutes. Temperature of FF tank and surrounding environment is maintained to 15° C.-25° C., preferably 18° C.-23° C. or more preferably 18° C.-20° C. After that, cross-linked tissue is stored in a 0.625% aqueous Glutaric dialdehyde buffer solution for a period of 6 days-10 days, preferable 7 days-9 days or more preferably 08 days to enhance durability and stability of fixed tissue. Maintaining the temperature of fixation increases the rate of diffusion of the fixative into the tissue and to speed up the rate of chemical reaction between the fixative and tissue components such as —NH$_2$ groups of protein, thus it provide "integrated" and "durable" fixed bovine pericardial tissue. Glutaric dialdehyde reacts with the side-chains of proteins to form reactive hydroxy-methyl groups. Glutaric dialdehyde also reacts with some groups in unsaturated lipids.

The following Scheme 1 represents the fixation reaction.

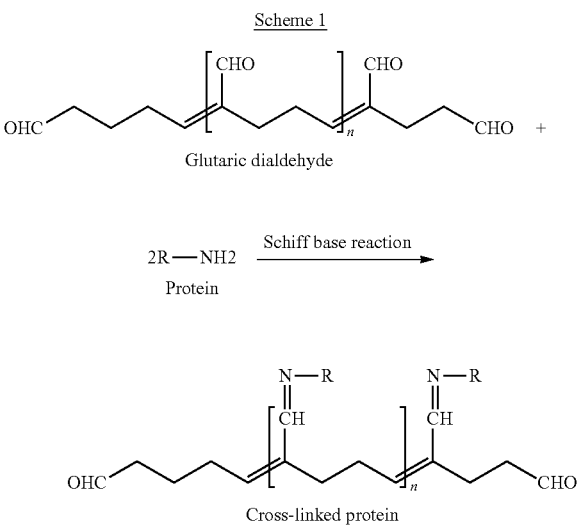

After chemical cross-linking process, fixed tissue is placed in a freshly prepared 0.625% Glutaric dialdehyde solution at low-oxygen environment till its further usage.

TABLE 2

Volume for the preparation of 1 liter
0.625% Glutaric dialdehyde aqueous solution

| Material | Composition for 01 Liter |
|---|---|
| $Na_2HPO_4 \cdot 7H_2O$ | 4.16 g |
| $KH_2PO_4$ | 0.61 g |
| NaCl | 7.89 g |
| Glutaric dialdehyde, 25% (w/V) approximation | 26.50 g |
| Water for Injection | 987.5 mL |

Laser Cutting of Fixed Tissue:

Laser cutting system is employed for the cutting of fixed tissue leaflet used for the heart valve fabrication.

Figure 4:
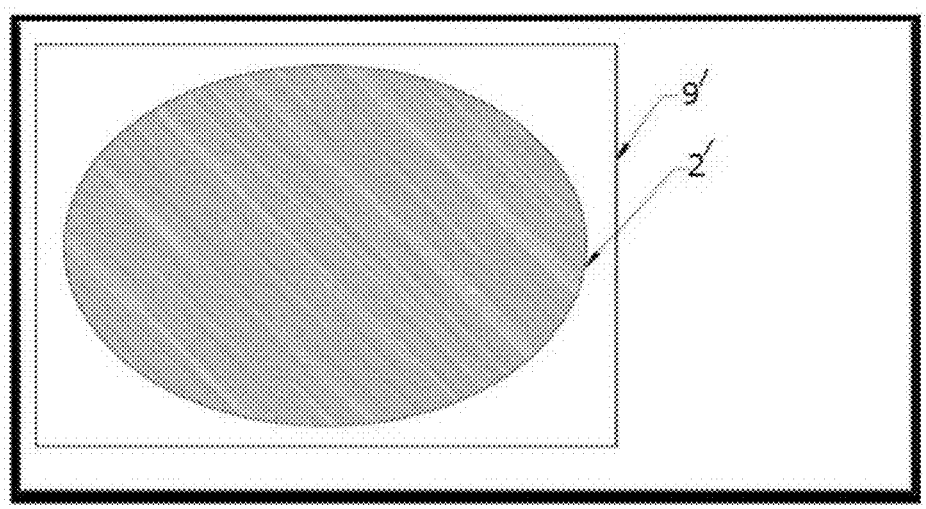
FIG. 4 is a perspective view of SS laser cutting tray, in accordance to exemplary embodiment of invention.

FIG. 4 shows the laser cutting tray, in which an SS tray (9') is provided for laser cutting the fixated tissue (2').

The method of cutting material employs a plotted laser cutting system in low-oxygen environment. The laser cutting system is computer controlled and includes a laser with a motion system. The laser precisely cuts tissue according to a predetermined pattern as designated by the computer which matches the criteria specified in heart valve leaflet design. During laser cutting, the laser energy is transformed into thermal energy, thus produces the specific shape leaflet and can be positioned in a heart valve frame to construct device.

Figure 5:
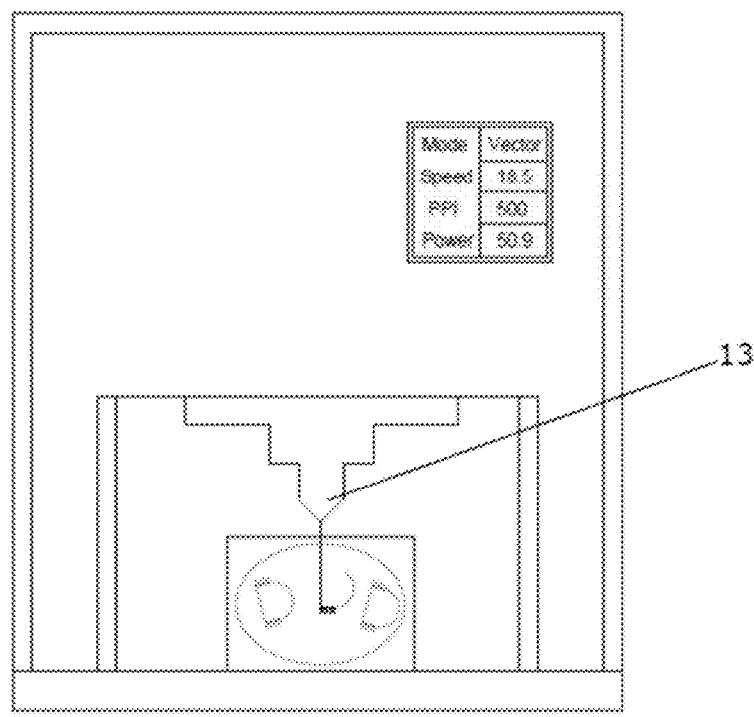
FIG. 5 illustrates view of laser beam irradiated over circular fixed tissue positioned on SS tray for tissue leaflet laser cutting process, in accordance to exemplary embodiment of invention.

As shown in FIG. 4, a fixed pericardium tissue is placed over SS laser cutting plate and source of laser beam (13) as shown in FIG. 5, is supplied under low-oxygen environment.

During laser cutting process, smooth surface of tissue is placed upside and in direct contact with laser beam. It prevents burning effect on fixed tissue and enhances edge to edge cutting of tissue thus involves in precise cutting of fixed tissue leaflet and reduces the risk of thrombosis. After laser cutting process, fixed tissue leaflets are rinsed with basic salt solution/0.9% chilled saline solution to eliminate traces under low-oxygen environment i.e. at 8-10% oxygen content and working area temperature is 18-20° C. Repeated washing step of laser cut tissue is carried out to avoid any unnecessary contamination. After saline washing step, laser cut tissue is rinsed with 0.625% aqueous Glutaric dialdehyde solution three times to remove traces of burned debris present at the edge of laser cut tissue. Also, rinsing with fixative solution reduces toxic elements generated while laser cutting step and removes dead colonies or other toxins, etc. Once laser cut leaflets are rinsed, it is again immersed in 0.625% Glutaric dialdehyde buffered solution at low-oxygen environment till its further use i.e. heart valve fabrication. Storage of laser cut tissue leaflet in same solution will engaged the basic characteristics and properties of tissue. The laser cut bovine pericardium leaflet thickness is maintained to 0.32 mm to 0.48 mm for heart valve fabrication and for surgical vascular reconstruction and repair.

TABLE 3

Laser cutting parameters
Laser Cutting Parameters

| Mode: | Vector Mode |
|---|---|
| Power: | 50.3% |
| Speed: | 18% |

Storage of Laser Cut Tissue:

The laser cut bovine pericardium is stored into a 0.625% Glutaric dialdehyde to keep moist and stored under low-oxygen environment at oxygen content 5-15%, preferably 8-10% and temperature 8-10° C. In a preferred embodiment, the laser cut bovine pericardium is stored at 8-10° C. temperature under vacuum sealed storage jar with 80 ml of 0.625% Glutaric dialdehyde solution for the storage purpose under low-oxygen environment till its further use.

AAS Treatment of Laser Cut Tissue Leaflets:

Phospholipids of biological tissue can act as a substrate for calcification thus reduces shelf life of tissue so various alcohol solutions in combination with aldehyde and surfactant are used to eliminate these calcifiable materials. In a preferred embodiment, ethanol is used to extract phospholipids in combination of aldehyde i.e. Formaldehyde and surfactant e.g. Tween-80.

In some exemplary embodiments, the other low-molecular weight alcohols such as methanol and isopropanol are also incorporated to effectively diminish calcification of laser cut tissue leaflets, which increases the stability, integrity and performance of bioprosthesis. Phosphorus, which is present inside the phospholipids are the potential binding site for the calcium to extract the phospholipids will mitigate the in-vivo calcification after implantation. As AAS contains alcohols which has similar structures with phospholipids and thus extracts from the laser cut tissue leaflets. Longer chain alcohols have a more similar structure with phospholipids, and they are known to replace phospholipids molecules, thus removing phospholipids molecules more efficiently. Removing phospholipids and lipid content also reduces cholesterol uptake from body thus avoids calcification which is major drawback of biological tissue. The use of AAS acts as an anti-calcification treatment and a bio-burden reduction step enhance shelf-life of bioprosthesis.

i. Role of Formaldehyde:

Formaldehyde is a material from cross-linking categories having single aldehyde moiety. It also has sterilant property thus acts as sterilant.

In some exemplary embodiments, the cross-linker is not limited to formaldehyde or Glutaric dialdehyde, but it can be selected from various categories such as, Carbodiimides, epoxides and other combination with aldehydes e.g. Glyceraldehyde, etc.

ii. Role of Ethanol:

Tissue treatment with organic solvents (ethanol, octanol, and octanediol) is incorporated to remove residual phospholipid content which is binding substrate for the calcium.

iii. Role of Polysorbate-80:

Polysorbate 80/Tween-80 is a non-ionic surfactant and emulsifier derived from polyethoxylated sorbitan and oleic acid. A surfactant is characterized by its tendency to adsorb at surfaces and interfaces. Tween-80 also removes acidic type of phospholipids from the tissue which is directly linked with tissue shelf life.

In another exemplary embodiment, the surfactant can be selected from the category of anionic surfactant or a non-ionic surfactant or a mixture thereof. Various examples of anionic surfactants are sodium dodecyl sulfate, sodium dodecyl sulfoacetate and examples of non-ionic surfactants are octylphenoxy polyethoxy ethanol, polyoxyethylene, tween-80 or tween-60.

TABLE 4

| Volumes for AAS solution | |
|---|---|
| Chemical (Solute) | Total Volume (1 L) |
| $Na_2HPO_4$ | 2.40 g |
| $KH_2PO_4$ | 0.416 g |
| Polysorbate-80 | 12.00 ml |
| Ethanol (99.97%) | 243 ml |
| 37% Formaldehyde | 108.19 ml |
| Water For Injection | 637.0 ml |

The laser cut tissue leaflets are immersed in AAS solution for 1 hour to 20 hours at low-oxygen environment where the oxygen content is maintained in between 5-15%, preferably 8-10% inside the Polypropylene (PP) storage jar. During this immersion period, the AAS solution is maintained at a temperature of 25° C.-45° C. Increasing the temperature enhances the chemical reaction thus removes phospholipids, which is prone to calcification.

In preferred embodiments, the AAS solution is prepared under low-oxygen atmosphere; the laser cut tissue leaflets are further subjected to bio-burden reduction process which is also called as AAS treatment. The laser cut tissue is placed in a vacuum sealed storage jar containing approximately 50 ml-90 ml of AAS solution, more preferably 75-85 ml under orbital shaker for gentle fluid movement. This jar is placed in orbital shaker at temperature of 25° C. to 45° C., more preferably 37° C. to 40° C. with gentle fluid movement for the period of 3 hours-6 hours. Due to gentle shaking, the bioburden reduction process is typically completed within short span of period. After treatment, the AAS treated (fixed) tissue is washed with de-ionized water or saline solution or phosphate buffer saline and further stored in 0.625% Glutaric dialdehyde solution under low-oxygen environment to maintain structural integrity and properties of fixed bovine pericardial tissue.

Figure 6:
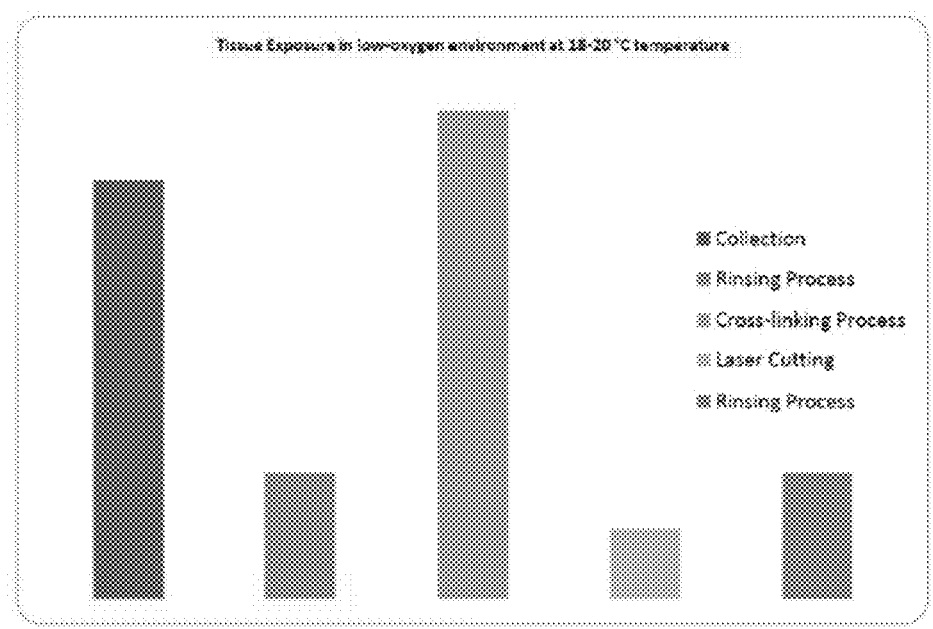
FIG. 6 is a bar diagram showing fixed tissue exposure time during processing, in accordance to exemplary embodiment of invention.

The fixed tissue is further utilized for the heart valve fabrication under controlled environmental condition i.e. under Laminar Air Flow (LAF). During fabrication of heart valve, the fixed tissue must be kept moist at all time, a saline flow sprinkled at regular interval which keeps tissue moist during fabrication process. The heart valve or bioprosthesis is then sterilized using Liquid Chemical (LC) sterilization process. The exposure time from tissue collection to fixation process at temperature between 18-20° C. is shown in FIG. 6. Exposure time under low-oxygen environment prevents morphological, chemical properties of tissue thus enhance integrity of fixed bovine pericardial tissue/bioprosthesis. The sterilized bioprosthesis is then packed and stored in low-oxygen environment to enhance stability of the bioprosthesis.

WORKING EXAMPLE 1

Fresh bovine hearts, with pericardium intact, collected from the FDA approved abattoir where the history and data of an animal is maintained as per standard and regulatory norms i.e. as ISO 13485 and ISO 22442. The fresh pericardial tissue is dissected and removed from the heart by cutting along the base of the heart, leaving the remaining tissue intact. The raw pericardium tissue having uniform thickness is transported to the laboratory in buffered saline. The fresh tissue is rinsed, and trimmed of external fat, adherent material in the laboratory.

Collected pericardial tissue is rinsed with chilled 0.9% saline solution by putting the tissue in stainless steel (SS) bath at room temperature & normal-oxygen environment of the air with humidity of 55%. Initially, 100 ml of chilled 0.9% saline solution is poured in a stainless steel bath and placed bovine pericardium which is already trimmed and washed previously while collection. Then, pericardium tissue is rinsed repeatedly till all debris and remaining fatty material washed off. After multiple rinsing, fresh chilled saline solution of volume 500 ml is again poured in SS bath and then rinsed tissue from both surface of tissue and transported for the cross-linking process. 5 litre of aqueous 0.625% Glutaric dialdehyde ($CHO(CH_2)_3CHO$) solution as per table 5 is freshly prepared and then vacuum filtered at normal-oxygen environment of air to remove any unwanted debris. 10 pieces of rinsed pericardial tissue is positioned in a fixation frame. Fixative solution is poured in fixative bath and 10 pieces of pericardium are placed therein. Circulatory pump is connected to the FF tank for proper circulation of cross-linking solution. The flow rate is maintained to 1.3 L/minute –2.2 L/minute. Tissue immersion period is set for 35 minutes at 18° C.-20° C. temperature at normal-oxygen environment of atmosphere. After that, cross-linked tissue is stored in a 0.625% aqueous Glutaric dialdehyde buffer solution for a period of 8 days. Further, it is laser cut into leaflets and processed to AAS treatment to remove bioburden.

TABLE 5

| Volume for the preparation of 5 liter 0.625% Glutaric dialdehyde aqueous solution | |
|---|---|
| Material | Composition for 05 Litre |
| $Na_2HPO_4 \cdot 7H_2O$ | 20.80 g |
| $KH_2PO_4$ | 3.05 g |
| NaCl | 39.45 g |
| Glutaric dialdehyde, 25% (w/V) approximation | 132.50 g |
| Distilled Water | 4937.50 mL |

The cross-linked tissue is additionally processed for the bioburden reduction step to remove unwanted debris, dead colonies, toxins and extracts cholesterol uptake thus reduces calcification and enhances the integrity and so the shelf life of fixed pericardium tissue. AAS solution is prepared under dry cabinet at normal-oxygen environment. The cross-linked tissue is placed in a vacuum sealed storage jar containing approximately 50 ml-90 ml of AAS solution, more preferably 80 ml under orbital shaker for gentle fluid movement. This jar is placed in orbital shaker at temperature of 37° C. to 40° C. with gentle fluid movement for 03 hours. After completion of treatment, the AAS treated (Fixed) tissue is washed with de-ionized water or saline solution or phosphate buffer saline and stored in 0.625% Glutaric dialdehyde solution.

Resulting tissue is further stored in freshly prepared 0.625% Glutaric dialdehyde solution at various temperature conditions as follows;
1. Fixed tissues are stored in 0.625% Glutaric dialdehyde solution at 25-30° C. in low-oxygen environment.
2. Fixed tissues are stored in 0.625% Glutaric dialdehyde solution at 25-30° C. in normal-oxygen environment of atmosphere.
3. Fixed tissues are stored in 0.625% Glutaric dialdehyde solution at 8-10° C. in low-oxygen environment.
4. Fixed tissues are stored in 0.625% Glutaric dialdehyde solution at 8-10° C. in normal-oxygen environment of atmosphere.

The fixed tissues are tested periodically for its mechanical strength (tissue tensile strength) at interval of initial, 03 months, 06 months, 09 months and 12 months. The results are provided in Table 6 below.

TABLE 6

All tissue processes are performed under normal-oxygen environment of air
Fixed Tissue Tensile Strength (N)

| Time Interval, Months | Stored at 25-30° C. Temperature | | Stored at 8-10° C. Temperature | |
|---|---|---|---|---|
| | Low-oxygen Environment | Normal-oxygen Environment | Low-oxygen Environment | Normal-oxygen Environment |
| Initial | 12.52 | 12.52 | 12.52 | 12.52 |
| 03 months | 12.41 | 11.79 | 12.49 | 12.21 |
| 06 months | 12.03 | 11.29 | 12.46 | 11.41 |
| 09 months | 11.48 | 10.21 | 12.24 | 10.39 |
| 12 months | 09.83 | 08.01 | 11.03 | 09.13 |

As per data illustrated above, it has been concluded that the fixed tissue which is stored at 8-10° C. temperature with low-oxygen environment has better tissue stability, integrity and durability.

WORKING EXAMPLE 2

Fresh bovine pericardium is collected from the TSE/BSE free animal whose upper age limit is less than 24 months at FDA approved abattoir. The heart pericardium is dissected as per ISO standards i.e. ISO22442 and separated from the heart under continuous shower of 0.9% chilled saline solution. The fresh pericardium tissue having identical thickness is transported to the laboratory in chilled saline to sustain electrolytic balance in living cells to evade putrefactive changes in tissue. The raw tissue is then rinsed, and trimmed out external fat, blood vessels and other adherent material in the laboratory under low-oxygen cabinet with continuous shower of chilled saline over tissue. The resulting tissue surface is inspected for holes, cracks and other debris. Approved quality raw pericardium tissue is further stored under low-oxygen environment to prevent oxidative damage to the tissue and transported for the cross-linking process in the laboratory.

Flat flange tank assembly equipped with low-oxygen environment and temperature sensor is used for improved cross-linking process to enhance fixation capabilities and competence of tissue. Low-oxygen environment is maintained inside the FF tank i.e. oxygen content of surrounding environment is 8-10% and working temperature is kept in between 18-20° C. Low-oxygen chamber aid in preservation the natural elasticity of the collagen matrix and enhances cross-link stability of collagen molecules. Freshly prepare 5 litre of aqueous 0.625% Glutaric dialdehyde (CHO(CH$_2$)$_3$CHO) solution under low-oxygen atmosphere cabinet to prevent degradation and oxidative reaction of Glutaric dialdehyde solution and then vacuum filtered to remove any unwanted particles. 10 pieces of pericardial tissue is positioned in a fixation frame to hold the tissue in stretch frame. Pour fixative solution in FF tank and place 10 pieces of pericardium. FF tank is further connected to pump for cross-linking solution circulation and 02 analyser and temperature sensor is attached. The flow rate is maintained between 1.3 L/minute and 2.2 L/minute. Tissue immersion period is set for 35 minutes at 18° C.-20° C. temperature. After that, cross-linked tissue is stored in a 0.625% aqueous Glutaric dialdehyde buffer solution for a period of 08 days in low-oxygen environment. The cross-linked tissue is additionally processed for the bioburden reduction step to remove unwanted debris, dead colonies, toxins and extracts phospholipids, reduce cholesterol uptake thus inhibit calcification and enhances integrity of fixed pericardium tissue. The tissue is placed in a vacuum sealed storage jar containing approximately 50 ml-90 ml of AAS solution, more preferably 80 ml under orbital shaker for gentle fluid movement. This jar is placed in orbital shaker at temperature of 37° C. to 40° C. with gentle fluid movement for 03 hours. After treatment, the AAS treated (Fixed) tissue is washed with de-ionized water or saline solution or phosphate buffer saline and stored in 0.625% Glutaric dialdehyde solution at various conditions as mentioned below.

1. Fixed tissues are stored in 0.625% Glutaric dialdehyde solution at 25-30° C. with low-oxygen environment.
2. Fixed tissues are stored in 0.625% Glutaric dialdehyde solution at 25-30° C. with normal-oxygen environment of atmosphere.
3. Fixed tissues are stored in 0.625% Glutaric dialdehyde solution at 8-10° C. with low-oxygen environment.
4. Fixed tissues are stored in 0.625% Glutaric dialdehyde solution at 8-10° C. with normal-oxygen environment of atmosphere.

The fixed tissues are tested periodically for mechanical strength (Tissue tensile strength) at interval of initials, 03 months, 06 months, 09 months and 12 months. The results are provided in Table 7 below.

TABLE 7

All tissue processes are performed under low-oxygen environment
Fixed Tissue Tensile Strength (N)

| Time Interval, Month | Stored at 25-30° C. Temperature | | Stored at 8-10° C. Temperature | |
|---|---|---|---|---|
| | Low-oxygen Environment | Normal-oxygen Environment | Low-oxygen Environment | Normal-oxygen Environment |
| Initial | 16.98 | 16.98 | 16.98 | 16.98 |
| 03 months | 16.71 | 15.91 | 16.94 | 16.13 |
| 06 months | 15.99 | 14.36 | 16.89 | 15.55 |
| 09 months | 15.61 | 12.24 | 16.85 | 14.25 |
| 12 months | 14.87 | 11.34 | 16.83 | 13.82 |

As per data illustrated above, it has been concluded that the fixed tissue which is stored at 8-10° C. with low-oxygen environment has better tissue stability, integrity and durability in compare to fixed tissue which is processed at normal-oxygen environment of air and stored at same atmosphere. Based on above data, it is concluded that there is no significant changes observed in fixed tissue tensile property stored under low-oxygen environment and temperature of 8-10° C. during storage of 01 year period. During prolong period of storage, it is assumed that the tensile properties will retain so the fixed tissue maintain its integrity, stability and performance over a period of time.

Hence the processing of bovine pericardial tissue under low-oxygen environment as mentioned above provide resulting tissue which shows distinct advantage in its integrity with higher tensile strength, minimum cracks & ruptures, clean and smooth surface, light in colour thereby providing higher stability in compare to bovine tissue processed at normal-oxygen environment of air described in example 1. After that, processed fixed tissue under low-oxygen environment is further tested for in-vitro hemodynamic performance as per ISO-5840 by fabricating heart valve.

The invention has been described on the basis of some preferred embodiments and non-limiting examples. Various modifications are possible without departing from the scope of the invention as previously described and defined in the appended claims.

The invention claimed is:

1. A process for treatment to avert enzymatic degradation and tissue degeneration of bovine pericardium tissue, used for making bioprosthesis for implant application, comprising the steps of
collecting and harvesting raw bovine pericardial tissue;
rinsing the pericardial tissue with chilled saline solution;
chemically crosslinking the rinsed tissue to generate fixed tissue;
laser cutting said fixed tissue to produce tissue leaflet;
chemically treating said tissue leaflet with a solution comprising alcohol, aldehyde and surfactant, wherein one litre of the solution consists of: 2.40 g of $Na_2HPO_4$, 0.416 g of $KH_2PO_4$, 12.00 ml of Polysorbate-80, 243 ml of 99.97% ethanol, 108.19 ml of 37% formaldehyde and 637.0 ml of water for injection;
chemically sterilizing and storing the chemically-treated tissue leaflet to maintain structural integrity and characteristics; and wherein all the above steps are carried out in a low-oxygen environment and under controlled temperature, wherein said low-oxygen environment has an oxygen content of 5-15% and wherein the said controlled temperature is in the range of 18-20° C. during processing and 8-10° C. during storing.

2. The process as claimed in claim 1, wherein the low-oxygen environment has an oxygen content of 8-10%.

3. The process as claimed in claim 1, wherein rinsing with chilled saline solution follows chemical and physical treatment steps until sterilizing and storing.

4. The process as claimed in claim 3, wherein rinsing with chilled saline solution is carried out by providing a continuous shower of chilled saline solution under low-oxygen and controlled temperature environment.

5. The process as claimed in claim 1, wherein the chemical cross-linking is carried out using 0.625% glutaric dialdehyde buffered solution.

6. The process as claimed in claim 5, wherein the cross-linking step is carried out for 35 minutes.

7. The process as claimed in claim 1, wherein the chemical cross-linking is carried out with continuous circular flow of Glutaric dialdehyde at rate of 0.8 L/min.

8. The process as claimed in claim 7, wherein the cross-linking step is carried out for 35 minutes.

9. The process as claimed in claim 1, wherein storing the chemically-treated tissue leaflet is carried out using 0.625% Glutaric dialdehyde buffered solution.

10. A process for making bioprosthesis for implant application, comprising the steps of collecting and harvesting raw bovine pericardial tissue;
rinsing the pericardial tissue with chilled saline solution;
chemically crosslinking the rinsed tissue to generate fixed tissue;
laser cutting said fixed tissue to produce tissue leaflet;
chemically treating said tissue leaflet with a solution comprising alcohol, aldehyde and surfactant, wherein one litre of the solution consists of: 2.40 g of $Na_2HPO_4$, 0.416 g of $KH_2PO_4$, 12.00 ml of Polysorbate-80, 243 ml of 99.97% ethanol, 108.19 ml of 37% formaldehyde and 637.0 ml of water for injection;
chemically sterilizing and storing the chemically-treated tissue leaflet to maintain structural integrity and characteristics; and
fabricating a bioprosthesis from such stored chemically-treated tissue leaflet under moist condition using sprinkled saline flow;
wherein all the above steps are carried out in a low-oxygen and controlled temperature environment, wherein said low-oxygen environment has an oxygen content of 5-15% and wherein the said controlled temperature is in the range of 18-20° C. during processing and 8-10° C. during storing.

* * * * *